United States Patent
Dahlqvist et al.

(10) Patent No.: US 10,285,877 B2
(45) Date of Patent: May 14, 2019

(54) PACKAGING UNIT HAVING IMPROVED SEALING AND A USER PROMPTING DEVICE, AND A METHOD FOR FORMING SUCH A PACKAGING UNIT

(71) Applicant: SCA HYGIENE PRODUCTS AB, Göteborg (SE)

(72) Inventors: Conny Dahlqvist, Göteborg (SE); Ulrika Persson, Göteborg (SE); Sofia Ekstedt, Göteborg (SE)

(73) Assignee: ESSITY HYGIENE AND HEALTH AKTIEBOLAG AB, Gothenburg (SE)

(*) Notice: Subject to any disclaimer, the term of this patent is extended or adjusted under 35 U.S.C. 154(b) by 332 days.

(21) Appl. No.: 15/318,216

(22) PCT Filed: Jun. 13, 2014

(86) PCT No.: PCT/SE2014/050720
§ 371 (c)(1),
(2) Date: Dec. 12, 2016

(87) PCT Pub. No.: WO2015/190966
PCT Pub. Date: Dec. 17, 2015

(65) Prior Publication Data
US 2018/0042790 A1    Feb. 15, 2018

(51) Int. Cl.
*B65D 85/07* (2017.01)
*B65D 65/14* (2006.01)
(Continued)

(52) U.S. Cl.
CPC .... *A61F 13/5514* (2013.01); *A61F 13/15747* (2013.01); *A61F 13/551* (2013.01);
(Continued)

(58) Field of Classification Search
CPC ............ A61F 13/5514; A61F 13/15747; A61F 13/551; A61F 13/5611; B65D 27/12; B65D 27/24; B65D 85/07
(Continued)

(56) References Cited

U.S. PATENT DOCUMENTS 2,750,033 A * 6/1956 Pickens ............. A61F 13/55145
206/361
3,913,580 A   10/1975 Ginocchio
(Continued)

FOREIGN PATENT DOCUMENTS

EP    0 368 914 A1    5/1990
EP    0 841 049 A1    5/1998
(Continued)

OTHER PUBLICATIONS

Wikipedia, "Corona treatment", http://en.wikipedia.org/wiki/Corona_treatment, Mar. 16, 2015, 6 pages.
(Continued)

*Primary Examiner* — Chun Hoi Cheung
(74) *Attorney, Agent, or Firm* — Buchanan Ingersoll & Rooney PC (57) ABSTRACT

The present disclosure provides a packaging unit for hygiene articles and a method for forming such a unit. The packaging unit has a first packaging function as a packaging wrap for a non-used article, and a second disposal function as a disposal wrap for a used article. The packaging unit further comprises a user prompting device having a wrap-facing surface and a user-facing surface, wherein the user prompting device is permanently attached to the wrap such that at least a portion of the wrap-facing surface of the user prompting device is in contact with the inner surface of the
(Continued)

wrap. The user prompting device is arranged to prompt the user to employ the second disposal function of the packaging unit.

28 Claims, 3 Drawing Sheets

(51) Int. Cl.
| | |
|---|---|
| *B65D 27/24* | (2006.01) |
| *B65D 27/12* | (2006.01) |
| *A61F 13/15* | (2006.01) |
| *A61F 13/56* | (2006.01) |
| *A61F 13/84* | (2006.01) |
| *A61F 13/551* | (2006.01) |

(52) U.S. Cl.
CPC .......... *A61F 13/5611* (2013.01); *B65D 27/12* (2013.01); *B65D 27/24* (2013.01); *A61F 2013/8497* (2013.01); *B65D 65/14* (2013.01); *B65D 85/07* (2018.01)

(58) Field of Classification Search
USPC ............. 206/438, 494; 604/385.02, 389, 390
See application file for complete search history.

(56) References Cited

U.S. PATENT DOCUMENTS

| | | | |
|---|---|---|---|
| 3,957,569 A | 5/1976 | Freitag | |
| 5,167,739 A | 12/1992 | Hutchinson et al. | |
| 5,238,178 A | 8/1993 | Hutchinson et al. | |
| 5,375,764 A | 12/1994 | Sauerwine | |
| H1454 H | 6/1995 | Cucuzza et al. | |
| 5,462,166 A | 10/1995 | Minton et al. | |
| 5,567,260 A | 10/1996 | McFall | |
| 5,569,230 A | 10/1996 | Fisher et al. | |
| 5,591,153 A | 1/1997 | Mattingly, III | |
| 5,598,970 A | 2/1997 | Mudry et al. | |
| 5,769,837 A | 6/1998 | Parr | |
| 5,792,131 A | 8/1998 | Mizutani | |
| 5,868,727 A | 2/1999 | Barr et al. | |
| 6,003,760 A | 12/1999 | Abercrombie | |
| 6,015,934 A | 1/2000 | Lee et al. | |
| 6,039,242 A | 3/2000 | Tee | |
| 6,176,850 B1 | 1/2001 | Rosenfeld et al. | |
| 6,186,993 B1 | 2/2001 | Toyoshima et al. | |
| 6,203,512 B1 | 3/2001 | Farris et al. | |
| 6,234,229 B1 | 5/2001 | Tabuchi | |
| 6,322,106 B1 | 11/2001 | Mehta et al. | |
| 6,500,160 B2 * | 12/2002 | Mizutani | A61F 13/551 |
| | | | 206/440 |
| 6,923,321 B2 * | 8/2005 | Samolinski | A61F 15/001 |
| | | | 206/440 |
| 7,083,079 B2 | 8/2006 | Bethke | |
| 7,708,727 B2 | 5/2010 | Woltman et al. | |
| 8,231,590 B2 | 7/2012 | Zander et al. | |
| 8,900,210 B2 | 12/2014 | Drevik et al. | |
| 9,155,668 B2 * | 10/2015 | Dahl | A61F 13/5514 |
| 2003/0163109 A1 * | 8/2003 | Ohba | A61F 13/5514 |
| | | | 604/385.03 |
| 2003/0225390 A1 | 12/2003 | Vogt et al. | |
| 2003/0234069 A1 | 12/2003 | Coenen et al. | |
| 2004/0107676 A1 | 6/2004 | Murray | |
| 2004/0238393 A1 * | 12/2004 | Ohi | A61F 13/5611 |
| | | | 206/438 |
| 2005/0137553 A1 | 6/2005 | Bechyne et al. | |
| 2005/0198931 A1 | 9/2005 | Cesiro et al. | |
| 2006/0025739 A1 | 2/2006 | DiPalma et al. | |
| 2006/0137568 A1 | 6/2006 | MacDonald et al. | |
| 2007/0049891 A1 | 3/2007 | Clark, Jr. et al. | |
| 2007/0189644 A1 | 8/2007 | Murray | |
| 2008/0067803 A1 | 3/2008 | Tanigawa | |
| 2009/0082747 A1 | 3/2009 | Carlen et al. | |
| 2010/0175825 A1 | 7/2010 | Baldauf | |
| 2010/0298797 A1 | 11/2010 | Ehlenbach et al. | |
| 2011/0028933 A1 | 2/2011 | Fung et al. | |
| 2011/0034897 A1 * | 2/2011 | Nomoto | A61F 13/5513 |
| | | | 604/385.02 |
| 2012/0090071 A1 | 4/2012 | Umebayashi | |
| 2012/0283682 A1 | 11/2012 | Otsubo et al. | |
| 2013/0165888 A1 | 6/2013 | Kinoshita et al. | |
| 2013/0199956 A1 | 8/2013 | Hunter et al. | |
| 2014/0155852 A1 | 6/2014 | Nishimura et al. | |
| 2015/0112294 A1 * | 4/2015 | Dahl | A61F 13/5514 |
| | | | 604/385.02 |

FOREIGN PATENT DOCUMENTS

| | | |
|---|---|---|
| EP | 0 955 243 A2 | 11/1999 |
| EP | 2 589 356 A1 | 5/2013 |
| GB | 2 273 279 A | 6/1994 |
| JP | H09-322909 A | 12/1997 |
| JP | 2000-51272 A | 2/2000 |
| JP | 2003-199786 A | 7/2003 |
| JP | 2006-45417 A | 2/2006 |
| JP | 2009-73498 A | 4/2009 |
| JP | 2013-85818 A | 5/2013 |
| JP | 2015-514542 A | 5/2015 |
| WO | WO 88/10219 A1 | 12/1988 |
| WO | WO 89/00459 A1 | 1/1989 |
| WO | WO 95/00092 A1 | 1/1995 |
| WO | WO 97/34556 A2 | 9/1997 |
| WO | WO 00/45767 A1 | 8/2000 |
| WO | WO 03/030796 A1 | 4/2003 |
| WO | WO 2005/087167 A1 | 9/2005 |
| WO | WO 2010/071512 A1 | 6/2010 |
| WO | WO 2010/135566 A1 | 11/2010 |
| WO | WO 2012/102071 A1 | 8/2012 |
| WO | WO 2012/157621 A1 | 11/2012 |
| WO | 2013-095224 A | 6/2013 |
| WO | WO 2013/162430 A1 | 10/2013 |
| WO | WO-2013162430 A1 * 10/2013 ......... A61F 13/5514 |
| WO | 2 737 886 A1 | 6/2014 |
| WO | WO 2014/188239 A1 | 11/2014 |

OTHER PUBLICATIONS

International Search Report (PCT/ISA/210) dated Feb. 23, 2015, by the Swedish Patent Office as the International Searching Authority for International Application No. PCT/SE2014/050724.
Written Opinion (PCT/ISA/237) dated Feb. 23, 2015, by the Swedish Patent Office as the International Searching Authority for International Application No. PCT/SE2014/050724.
International Preliminary Report on Patentability (PCT/IPEA/409) dated Jun. 8, 2016, by the Swedish Patent Office as the International Searching Authority for International Application No. PCT/SE2014/050724.
International Search Report (PCT/ISA/210) dated Feb. 20, 2015, by the Swedish Patent Office as the International Searching Authority for International Application No. PCT/SE2014/050725.
Written Opinion (PCT/ISA/237) dated Feb. 20, 2015, by the Swedish Patent Office as the International Searching Authority for International Application No. PCT/SE2014/050725.
International Preliminary Report on Patentability (PCT/IPEA/409) dated Jun. 13, 2016, by the Swedish Patent Office as the International Searching Authority for International Application No. PCT/SE2014/050725.
International Search Report (PCT/ISA/210) dated Feb. 16, 2015, by the Swedish Patent Office as the International Searching Authority for International Application No. PCT/SE2014/050719.
Written Opinion (PCT/ISA/237) dated Feb. 16, 2015, by the Swedish Patent Office as the International Searching Authority for International Application No. PCT/SE2014/050719.
International Preliminary Report on Patentability (PCT/IPEA/409) dated Jun. 14, 2016, by the Swedish Patent Office as the International Searching Authority for International Application No. PCT/SE2014/050719.

(56) References Cited

OTHER PUBLICATIONS

European Patent Office Letter dated Mar. 27, 2015, for International Application No. PCT/SE2014/050719.
International Search Report (PCT/ISA/210) dated Feb. 11, 2015, by the Swedish Patent Office as the International Searching Authority for International Application No. PCT/SE2014/050720.
Written Opinion (PCT/ISA/237) dated Feb. 11, 2015, by the Swedish Patent Office as the International Searching Authority for International Application No. PCT/SE2014/050720.
Written Opinion of the International Preliminary Examining Authority (PCT/IPEA/408) dated Jun. 3, 2016, by the Swedish Patent Office as the International Searching Authority for International Application No. PCT/SE2014/050720.
Written Opinion of the International Preliminary Examining Authority (PCT/IPEA/408) dated Jul. 7, 2016, by the Swedish Patent Office as the International Searching Authority for International Application No. PCT/SE2014/050720.
European Patent Office Letter dated Aug. 24, 2015, for International Application No. PCT/SE2014/050720.
European Patent Office Letter dated Jun. 29, 2016, for International Application No. PCT/SE2014/050720.
International Search Report (PCT/ISA/210) dated Mar. 2, 2015, by the Swedish Patent Office as the International Searching Authority for International Application No. PCT/SE2014/050726.
Written Opinion (PCT/ISA/237) dated Mar. 2, 2015, by the Swedish Patent Office as the International Searching Authority for International Application No. PCT/SE2014/050726.
Written Opinion of the International Preliminary Examining Authority (PCT/IPEA/408) dated Jun. 3, 2016, by the Swedish Patent Office as the International Searching Authority for International Application No. PCT/SE2014/050726.
International Preliminary Report on Patentability (PCT/IPEA/409) date Jul. 12, 2016, by the Swedish Patent Office as the International Searching Authority for International Application No. PCT/SE2014/050726.
European Patent Office Letter dated Apr. 7, 2015, for International Application No. PCT/SE2014/050726.
International Search Report (PCT/ISA/210) dated Feb. 11, 2015, by the Swedish Patent Office as the International Searching Authority for International Application No. PCT/SE2014/050718.
International Preliminary Report on Patentability (PCT/IPEA/409) dated Jun. 8, 2016, by the Swedish Patent Office as the International Searching Authority for International Application No. PCT/SE2014/050718.
European Patent Office Letter dated Mar. 27, 2015, for International Application No. PCT/SE2014/050718.
Office Action dated Oct. 30, 2018, by the Colombian Patent Office in corresponding Colombian Patent Application No. NC2017/0000201 and a partial English Translation of the Office Action. (23 pages).
Office Action (Examination Report No. 1 for Standard Patent Application) dated Feb. 13, 2017, by the Australian Patent Office in corresponding Australian Patent Application No. 2014396900. (3 pages).
Ciba-Geigny AG (Durr's) Applications [1977] RPC 83. Published Feb. 17, 1977.
Section 2.9.2.8 of Australian Patent Manual of Practice & Procedure, titled "Printed Matter". Retrieved Feb. 19, 2017. <http://manuals.ipaustralia.gov.au/patents/national/patentable/2.9.2.8_printed_matter.htm>. (2 pages).
English Translation of Office Action (Decision to Grant) dated Jan. 30, 2018, by the Russian Patent Office in corresponding Russian Patent Application No. 2017100892/12(001424). (9 pages).
Office Action (Notice of Reasons for Rejection) dated Nov. 13, 2017, by the Japanese Patent Office in corresponding Japanese Patent Application No. 2016-572472 and English Translation of the Office Action. (6 pages).
The extended European Search Report dated Oct. 16, 2017, by the European Patent Office in European Patent Application No. 14894531.4-1308. (7 pages).

\* cited by examiner

PACKAGING UNIT HAVING IMPROVED SEALING AND A USER PROMPTING DEVICE, AND A METHOD FOR FORMING SUCH A PACKAGING UNIT

TECHNICAL FIELD

The present disclosure relates to a packaging unit for hygiene articles, comprising a wrap and a user prompting device. The present disclosure also relates to a method of forming a packaging unit comprising a wrap and a user prompting device.

BACKGROUND

Disposable hygiene articles, such as sanitary napkins and panty liners, are normally packaged individually in e.g. an easy wrap or a single wrap. Individual packages facilitate hygienic carrying of single articles for future use, e.g. in a handbag. The edges of the individual packages are often sealed by means of ultrasonic welding or heat welding. Further, the packaging units are often used both as a means for packaging an unused article and for disposal of the used article.

It is desirable that used articles of this kind can be disposed of discretely and hygienically. This may be particularly important when the user lacks the possibility to dispose of the used article immediately after the used article has been replaced, e.g. when there is no waste bin available in the toilet area. In this case, the user may need to put the used article in e.g. a handbag or backpack, which requires that the package is adequately sealed in order to avoid staining and odour.

One of the solutions addressing the disposal problem has been suggested in WO 2013/162430, describing a packaging unit being formed from a sheet having at least one folding axis dividing the sheet into a first region and a second region. The inner surface of the first region comprises an inner edge portion and an outer edge portion, wherein one of the portions is provided with adhesive, and the other of the portions is adhesive-free. Further, one of the inner and outer portions of the second region is either provided with adhesive or is adhesive-free in a complementary manner to the first region. Thus, when the sheet is folded about the folding axis, the edge portions carrying adhesive in the first region are brought in contact with the adhesive-free edge portions in the second region, and the edge portions carrying adhesive in the second region are brought in contact with the adhesive-free edge portions in the first region. The packaging unit disclosed in WO 2013/162430 has a first packaging function, wherein the packaging unit provides a tightly sealed package for a non-used article, and a second disposal function for hygienic keeping and disposing of the used hygiene article.

However, an average user may have difficulties in identifying the presence of a disposal function of a packaging unit. Failure to identify the disposal function of the packaging unit leads to incorrect, cumbersome and sometimes unsanitary disposal of a used hygiene article. It also leads to material waste, since the user may discard the packaging unit intended for disposal, and instead use some other material available to wrap the used article prior to disposal, such as toilet paper, a paper towel or a tissue.

Hence, there is a need for a packaging unit which can be used both for packaging a new hygiene article and for hygienic keeping and disposing of the used hygiene article, which is aesthetically appealing and which provides an easy and intuitive identification of the disposal function of the packaging unit.

SUMMARY

The present disclosure provides a packaging unit for hygiene articles and a method of forming a packaging unit, which substantially eliminates the drawbacks of the packaging units discussed above.

The present disclosure provides a packaging unit having a first packaging function as a packaging wrap for a non-used article, and a second disposal function as a disposal wrap for a used article. The packaging unit of the present disclosure provides a possibility of forming a tight package both for a new and a used article, thus keeping the new article sanitary and clean prior to use, and eliminating the risk of staining and odour when a used article is packaged. The packaging unit is easy to unfold and reseal, is aesthetically appealing, and provides an easy and intuitive identification of the disposal function of the packaging unit.

As used herein, the term "inner surface" refers to the surface of the packaging unit facing the product positioned inside the packaging unit, and the term "outer surface" refers to the surface opposite to the inner surface, i.e. the surface facing the ambient.

By the term "edge zone" is meant the portion of the packaging unit adjacent to the edges of the packaging unit. The width of an edge zone may be varied.

The term "inner edge portion" refers to the portion of the edge zone positioned towards the centreline of the packaging unit.

The term "outer edge portion" refers to the portion of the edge zone positioned towards the edge of the packaging unit.

The term "central portion" refers to the portion of the packaging unit excluding the edge zone.

By the term "single ply" is meant a packaging unit comprising a single ply of a coherent material. The examples of a single ply packaging unit may be a plastic film, such as a polyethylene film, a nonwoven material, a metallic foil or the like. A single ply material may be a non-homogenous material such as a plastic film material comprising integrated layers or a nonwoven material having varying fibre composition in different parts of the material. A single ply material as used herein does not comprise materials having separable layers.

By the term "laminate" is meant a packaging unit comprising at least two united separable plies of material that can be the same or different. In the context of the present disclosure, the laminate may for example be constituted of two separable plies of plastic film, a film and nonwoven, two plies of nonwoven or the like.

By the term "permanently attached" is meant two surfaces being in such a contact with each other that it is not possible to break the contact without affecting either or both surfaces.

"Releasably affixed" means two surfaces being bonded to each other such that the bond may be readily broken without affecting the surfaces.

By the term "resealable adhesive" is meant an adhesive that provides a non-permanent adhesive bond between two adherent surfaces, i.e. a bond that may be broken by applying a pulling force to the adherent, and recreated by applying a pressing force to the adherent.

The term "visible" means distinguishable by an unaided human eye.

The term "legible" means being capable of being read or deciphered and being understandable or recognizable based on appearance.

The packaging unit for hygiene articles according to the present disclosure comprises a wrap being formed from a sheet of material having an inner surface and an outer surface. The inner surface comprises an edge zone comprising an inner edge portion and an outer edge portion. The wrap has at least one first folding axis dividing the wrap into a first region and a second region. One of the inner edge portion and the outer edge portion of the edge zone of the first region is provided with a first resealable adhesive, and the other of the inner edge portion and the outer edge portion of the edge zone of the first region is adhesive-free. Further, one of the inner edge portion and the outer edge portion of the edge zone of the second region is provided with the first resealable adhesive, and the other of the inner edge portion and the outer edge portion of the edge zone of the second region is adhesive-free in a complementary manner to the edge zone of the first region, such that when the wrap is folded about the folding axis, the edge portions carrying resealable adhesive in the first region are brought in contact with the adhesive-free edge portions in the second region, and the edge portions carrying resealable adhesive in the second region are brought in contact with the adhesive-free edge portions in the first region.

As mentioned above, the packaging unit of the present disclosure has a first packaging function as a packaging wrap for a non-used article, and a second disposal function as a disposal wrap for a used article. The packaging unit according to the present disclosure further comprises a user prompting device having a wrap-facing surface and a user-facing surface, wherein the user prompting device is permanently attached to the wrap such that at least a portion of the wrap-facing surface of the user prompting device is in contact with the inner surface of the wrap. The user prompting device is arranged to prompt the user to employ the second disposal function.

The user prompting device of the present disclosure may be of any shape, size, colour or texture, as long as it prompts the user to employ the second disposal function of the packaging unit.

Thus, the user prompting device may have substantially the same shape as the hygiene article inside the packaging unit. The user prompting device will thus indicate to the user that the used hygiene article may be positioned over the user prompting device, followed by subsequent folding or rolling of the wrap, thus forming a tight package containing the used article and employing the second disposal function of the packaging unit.

The user prompting device may further comprise a user prompting means being visible and legible from the user-facing surface of the user prompting device. The user prompting means arranged such that it is visible and legible from the user-facing surface of the user prompting device has the advantage of being available to the user immediately after the new hygiene article has been removed from the packaging unit, i.e. when the user is most likely to need a wrapping material for disposal of a used article.

The user prompting means may be a text, a graphic, a symbol or a combination thereof. The user prompting means has to be legible from the user-facing surface of the user prompting device, i.e. the user has to be able to understand the meaning of the user prompting means by observing the user prompting device from the user-facing surface thereof.

The text of the user prompting means may comprise words such as "Roll, press, go", "Place used article here", "Please use as disposal wrap", "Use for safe disposal", or any other words which would indicate the presence of second disposal function of the packaging unit.

The user prompting means may comprise graphics showing how the second disposal function of the packaging unit is employed. For instance, the graphics of the user prompting means may illustrate the steps of employing the second disposal function of the packaging unit.

Further, the user prompting means may comprise symbols indicating the presence of the second disposal function of the packaging unit. Thus, the user prompting means may comprise an arrow, a cross or any other symbol or combination of symbols alerting the user of the presence of the second disposal function.

As mentioned above, the user prompting means may comprise a combination of text, graphics and symbols. Thus, the user prompting means may comprise the text "Roll, press, go" accompanied by corresponding graphics for each of the steps of employment of the second disposal function of the packaging unit.

The user prompting means may be printed on the user-facing surface of the user prompting device, on the wrap-facing surface of the user prompting device, or on both the user-facing surface and the wrap-facing surface of the user prompting device.

When the user prompting means is printed on the wrap-facing surface of the user prompting device, the user prompting means should be visible and legible from the user-facing side of the user prompting device. In order for the user prompting means to be visible from the user-facing surface of the user prompting device, the combination of the material of the user prompting device and the user prompting means should be chosen such that the user prompting device is sufficiently transparent, and the user prompting means is sufficiently distinct. In order for the user prompting means being printed on the wrap-facing surface of the user prompting device to be legible from the user-facing surface of the user prompting device, the text, graphics or symbols of the user prompting means should be printed in reverse. When such an embodiment is used, the user prompting means should not be visible through the outer surface of the wrap, since the user prompting means being visible in reverse from the outer surface of the wrap may impair the perception of the product as a whole comprising the packaging unit of the present disclosure when viewed from the outer surface of the wrap.

The user prompting means may be printed on both the user-facing surface and the wrap-facing surface of the user prompting device, for instance when it is desirable for the user prompting means to be visible both from the user-facing surface of the user prompting device, and from the outer surface of the wrap in order to inform the user of the presence of the second disposal function of the packaging unit, e.g. when packages containing hygiene articles wrapped into packaging units according to the present disclosure are being displayed on a store shelf, or prior to opening the packaging unit containing an unused hygiene article. When the user prompting means is printed on both the user-facing surface and the wrap-facing surface of the user prompting device, the user prompting device should be sufficiently opaque to prevent the user prompting means printed on the user-facing surface of the user prompting device from being visible from the outer surface of the wrap, and to prevent the user prompting means printed on the wrap-facing surface of the user prompting device from being visible from the user-facing surface of the user prompting device, thus ensuring legibility of the user prompting means both from the user-facing surface of the user prompting means, and from the outer surface of the wrap, provided that at least a portion of the wrap material corresponding to the portion of the user prompting device comprising the user prompting means is sufficiently transparent to allow the user prompting means printed on the wrap-facing surface of the user prompting device to be visible from the outer surface of the wrap.

The user prompting device according to the present disclosure may be any piece of material permanently attached to the inner surface of the wrap. Preferably, the user prompting device comprises a release liner. The release liner may be manufactured from any suitable material known to the person skilled in the art, such as paper, non-woven or plastic film material.

It is sufficient that a portion of the user prompting device is attached to a portion of the inner surface of the wrap to thereby be in contact therewith. Thus, only a portion of the user prompting device may be attached to the central portion of the inner surface of the wrap. Alternatively, the entire wrap-facing surface of the user prompting device may be attached to the inner surface of the wrap. Preferably, two or three portions of the user prompting device are attached to the inner surface of the wrap, wherein the portions of the wrap-facing surface of the user prompting device being attached to the inner surface of the wrap are spaced apart along the longitudinal direction of the user prompting device. The user prompting device may be permanently attached to the wrap by means of a second adhesive. The second adhesive may be of any type known to a person skilled in the art, such as a construction adhesive.

In order to provide a user prompting device that is easily detachable from the garment-affixing adhesive that may be present on the garment-facing surface of the hygiene article, the user prompting device may be silicone-coated on the user-facing surface of the user prompting device. When the user-facing surface of the user prompting device is provided with a silicone coating, and it is at the same time desirable to print the user prompting means on the user-facing surface of the user prompting device, the user prompting means should be printed beneath the silicone coating, since the material of the user prompting means, e.g. ink, may lack the ability to adhere to the silicone coating, resulting in the user prompting means becoming smeared, and thus illegible, upon contact with any surface.

As mentioned above, the size of the user prompting device may vary, provided that the user prompting device prompts the user to employ the second disposal function of the packaging unit. Preferably, the longitudinal extension of the user prompting device is 60-100% of the longitudinal extension of the wrap. The transverse extension of the user prompting device may be 30-90% of the transverse extension of the wrap. The user prompting device having the above-mentioned dimensions is readily noticeable by the user. Further, the user prompting device having the above-mentioned dimensions may be used as a release liner.

A suitable first resealable adhesive to be used with the packaging unit of the present disclosure is a pressure-sensitive adhesive having an unlimited open time, meaning that the adhesive can bond to another substrate at any time. The first resealable adhesive used with the packaging unit is one which has a very high self-adhesion but which can be readily separated or released from other materials, such as plastic materials or paper which has been treated with a release agent. A major advantage of the packaging unit according to the present disclosure is that it can be completely unfolded when a new hygiene article is about to be taken out. In contrast thereto, prior art packages having adhesively sealed edges with adhesive-coated edge portions being in contact with each other have too high adhesive strength of the adhesively sealed edges, and any attempt to completely unfold the package generally leads to tearing and breakage of the packaging unit, making it unusable for discrete and hygienic disposal of the used article. As the adhesive-coated edge portions of the packaging unit of the present disclosure are not in contact with each other when the packaging unit is folded, the packaging unit can be readily opened and resealed, providing a tight disposal package. At the same time, the tensile strength of the adhesively sealed edges of the packaging unit using the adhesive pattern of the present disclosure is sufficient to provide a tight package for both a new and a used article, and low enough to provide a readily-opened package.

The geometrical shape of the wrap can vary depending on the type of the hygiene article to be packaged. The wrap may be circular, triangular, square, rectangular, or any other shape suitable for the hygiene article to be packaged. It is desirable, however, that the wrap has at least one symmetry axis.

As mentioned above, the packaging unit comprises at least one folding axis. The number of folding axes may vary depending on how the packaging unit is intended to be folded. It is preferred that the packaging unit comprises between one and three folding axes.

The prevailing shape of the wrap of material for forming a packaging unit is square or rectangular. Such a wrap according to the present disclosure has side edges, referred to herein as longitudinal edges, a first and a second transverse edge and corner portions, the edge zones of the first and second regions of the wrap of material being arranged along the longitudinal edges. The edge portions covered with the first resealable adhesive and the adhesive-free portions are thus positioned along the longitudinal edges. Preferably, the resealable adhesive arranged at the outer edge portions may be positioned such that it extends all the way to the longitudinal edges of the sheet.

The width of the adhesive-covered edge portions may be varied depending on the adhesive strength desired. The wider the adhesive-covered edge zones, the stronger the sealing. The width of the adhesive-covered edge portions may be same or different in the different regions.

Preferably, the length of the adhesive-covered edge portions in each region is equal to the length of each region. Also, the length of the adhesive-covered edge portions in each region may be shorter than the length of each region.

The sheet of material may comprise a first and a second transverse edge zones, being arranged along the transverse edges of the sheet of material from which the wrap according to the present disclosure is formed. The first transverse edge zone is provided at the transverse edge of the first region. The positioning of the second transverse edge zone depends on the number of folding axes. When the wrapping sheet comprises one folding axis, the second transverse edge zone is arranged at the transverse edge of the second region. When the wrapping sheet comprises two folding axes, the second transverse edge zone is arranged at the transverse edge of the third region, and so forth.

Preferably, the first transverse edge zone of the first region of the wrap is provided with the resealable adhesive, while the second transverse edge zone of the wrap is adhesive-free. When the wrap comprises one folding axis, it is conceivable that a portion of the first transverse edge zone of the first region is provided with the first resealable adhesive, while the remaining portion of the first transverse edge zone of the first region is adhesive-free, and a portion of the second transverse edge zone of the second region is provided with the first resealable adhesive, while a remaining portion of the second transverse edge zone of the second region is adhesive-free in a complementary manner to the transverse edge zone of the first region. Thus, when the packaging unit is folded about the first folding axis, the transverse edge portion carrying the resealable adhesive in the first region is brought in contact with the adhesive-free transverse edge portion in the second region, and the transverse edge portion carrying the first resealable adhesive in the second region is brought in contact with the adhesive-free transverse edge portion in the first region. Also, both the first and the second transverse edge zones of the packaging unit may be provided with the resealable adhesive, when the packaging unit comprises at least two folding axes.

In order to facilitate opening, at least one of the corner portions may be free from the first resealable adhesive such that a gripping tab is formed.

As mentioned above, one of the most common folding patterns for individually wrapped hygiene products is so called e-folding. In this case the wrap has two folding axes, dividing the wrap into a first region, a second region and a third region. The packaging unit may then be formed, wherein the wrap is folded along the folding axes with the first, second and third regions in an overlapping configuration.

According to the present invention, when the wrap has two folding axes dividing the wrap into a first, a second and a third region, and the packaging unit is formed by e-folding. The edge portion of the edge zone of the third region provided with the first resealable adhesive corresponds to the edge portion of the edge zone of the first region provided with the first resealable adhesive, and is complementary to the edge portion of the edge zone of the second region provided with the first resealable adhesive. Thus, a chessboard pattern of the first resealable adhesive is formed along each of the longitudinal edge zones.

The wrap for forming a packaging unit may be a single ply sheet of any suitable material known to the person skilled in the art, such as polyethylene or polypropylene film or nonwoven. The wrap may also be a laminate comprising at least two distinct layers. Laminates suitable for packaging of hygiene articles are assumed to be known to the person skilled in the art, and are not in any way limiting for the present disclosure.

If desired, the wrap for forming a packaging unit according to the present disclosure may be opaque in order to disguise the contents of the packaging unit, which is particularly important if the used article wrapped into the packaging unit of the present disclosure cannot be disposed of immediately after replacement. When the wrap is opaque, the user prompting means may not be visible through the outer surface of the wrap. This may be advantageous when it is desirable to prevent the user prompting means, that may be visible from the wrap-facing surface of the user prompting means in reverse, from being visible from the outer surface of the wrap. The user prompting means visible in reverse from the outer surface of the wrap would be illegible, which may be perceived as confusing and irritating by the user. Further, in cases when the wrap comprises print, e.g. for attracting the user's attention and improving the user's mood, the user prompting means visible in reverse from the outer surface of the wrap may detract from the design of the wrap.

The wrap of material forming a packaging unit according to the present disclosure may comprise an odour-inhibiting or odour-neutralising substance. Such a substance may be applied in any suitable manner known to the person skilled in the art, e.g. as a coating, activatable microcapsules, impregnated patches or the like. Further, such a substance may be arranged on or in the user prompting device. Preferably, such a substance is integrated into the user prompting device in order to avoid the need for an additional material.

It is conceivable that the wrap for forming a packaging unit according to the present disclosure may be stretchable or expandable, which may be advantageous if the hygiene article is greatly deformed during use, and may thus be difficult to wrap without deforming the packaging unit.

The first resealable adhesive used in the present disclosure may be a pressure-sensitive hotmelt adhesive, such as Lunatack® D656 BD 19 available from H. B. Fuller.

The packaging unit according to the present disclosure may be used for forming a packaged disposable hygiene article. The hygiene article may be releasably affixed to the user prompting device, either by means of a third resealable adhesive or by any other suitable fastening means known to the person skilled in the art, e.g. hook-and-loop fastening means.

The packaging unit for hygiene articles according to the present disclosure, wherein the packaging unit has a first packaging function as a packaging wrap for a non-used article, and a second disposal function as a disposal wrap for a used article, may be manufactured by a method comprising the steps of:

a. providing a wrap having an inner surface and an outer surface, the inner surface comprising an edge zone comprising an inner edge portion and an outer edge portion, the wrap having at least one first folding axis, the first folding axis dividing the wrap into a first region and a second region, wherein the first region comprises a first central portion, and the second region comprises a second central portion;

b. providing one of the inner edge portion and the outer edge portion of the edge zone of the first region with a first resealable adhesive, such that the other of the inner edge portion and the outer edge portion of the edge zone of the first region is adhesive-free;

c. providing one of the inner edge portion and the outer edge portion of the edge zone of the second region with the first resealable adhesive, such that the other of the inner edge portion and the outer edge portion of the edge zone of the second region is adhesive-free in a complementary manner to the edge zone of the first region;

d. providing the inner surface of the packaging unit with a user prompting device having a wrap-facing surface and a user-facing surface and arranged to prompt the user to employ the second disposal function.

Preferably, steps b and c, i.e. the steps of applying the first resealable adhesive to the edge portions of the wrap, occur simultaneously, which is advantageous for the manufacturing process.

The user prompting device may be attached to the inner surface of the wrap by any suitable means known to the person skilled in the art, e.g. ultrasonic welding or mechanical fastening. Preferably, the user prompting device is attached to the inner surface of the wrap by means of a second adhesive. Thus, the method of the present disclosure may further comprise the steps of:

e. providing at least one of the first central portion of the first region and the second central portion of the second region of the wrap with a second adhesive;

f. bringing the wrap-facing surface of the user prompting device in contact with the inner surface of the wrap such that at least a portion of the wrap-facing surface of the user prompting device becomes permanently attached to the inner surface of the wrap in at least the first and the second central portions being provided with the second adhesive by means of the second adhesive;

wherein steps e and f occur after step a but before step d.

Preferably, step e occurs simultaneously with steps b and c, i.e. the first and the second adhesives are applied during a single manufacturing step prior to attaching the wrap-facing surface of the user prompting device to the inner surface of the wrap.

The method of the present disclosure may further comprise a step g of releasably affixing a hygiene article to the user-facing surface of the user prompting device. The hygiene article may be attached to the user-facing surface of the user prompting device either before or after the wrap-facing surface of the user prompting device is attached to the inner surface of the wrap, i.e. before step d, or after step f. The hygiene article may be attached to the user-facing surface of the user prompting device by means of a third resealable adhesive, which may be a pressure-sensitive adhesive that is used for affixing the hygiene article to a garment. If the third adhesive is used, the method according to the present disclosure may comprise step i of providing the user-facing surface of the user prompting device with a third resealable adhesive, wherein step i occurs immediately before step g.

The method of the present disclosure may further comprise the step of folding the wrap about the first folding axis, such that the edge portions carrying the first resealable adhesive in the first region are brought in contact with the adhesive-free edge portions in the second region, and the edge portions carrying the first resealable adhesive in the second region are brought in contact with the adhesive-free edge portions at the first region.

When the packaging unit according to the present disclosure comprises a first and a second folding axes, dividing the wrap into the first region, the second region and a third region, the method may further comprise the steps of:

j. providing a portion of the edge zone of the third region with the first resealable adhesive;

k. folding the wrap about the second folding axis such that the inner surface of the third region is brought in contact with the outer surface of the first region;

wherein step j occurs after step a but before step d, and step k occurs after step h.

Preferably, step j occurs simultaneously with steps b and c, i.e. the first resealable adhesive is applied simultaneously to the edge portions in all three regions.

It should be noted that when a packaging unit comprising at least two folding axes, i.e. at least three regions, is folded, the adhesive-covered edge portions of the first region are brought into contact with the adhesive-free portions of the second region, and the adhesive-covered portions of the second region are brought into contact with the adhesive-free portions of the first region. The subsequently folded third region is folded over the outer surface of the first region forming a lid, and the adhesive-covered edge portions of the third region are thus brought into contact with the adhesive-free outer surface of the first region. In this particular case, the folding order may be reversed, i.e. the adhesive-covered edge portions of the second region may be brought in contact with the adhesive-free portions of the third region, and the adhesive-covered portions of the third region may be brought in contact with the adhesive-free portions of the second region. The lid is formed by folding the first region over the outer surface of the third region. The adhesive pattern according to the present disclosure thus has the advantage of giving the user a possibility to fold the packaging unit in any order, yet still obtain a liquid- and odour-tight package, ensuring that the used article is disposed in a discrete and hygienic manner. Further, when the packaging unit of the present disclosure is used for disposal, the user may choose to roll up the packaging unit instead of folding it. According to the present disclosure, the second disposal function of the packaging unit is clearly indicated to the user by the user prompting device.

BRIEF DESCRIPTION OF THE DRAWINGS

Embodiments will now be described by way of example with reference to the accompanying drawings, of which.

DETAILED DESCRIPTION OF PREFERRED EMBODIMENTS

Figure 1:
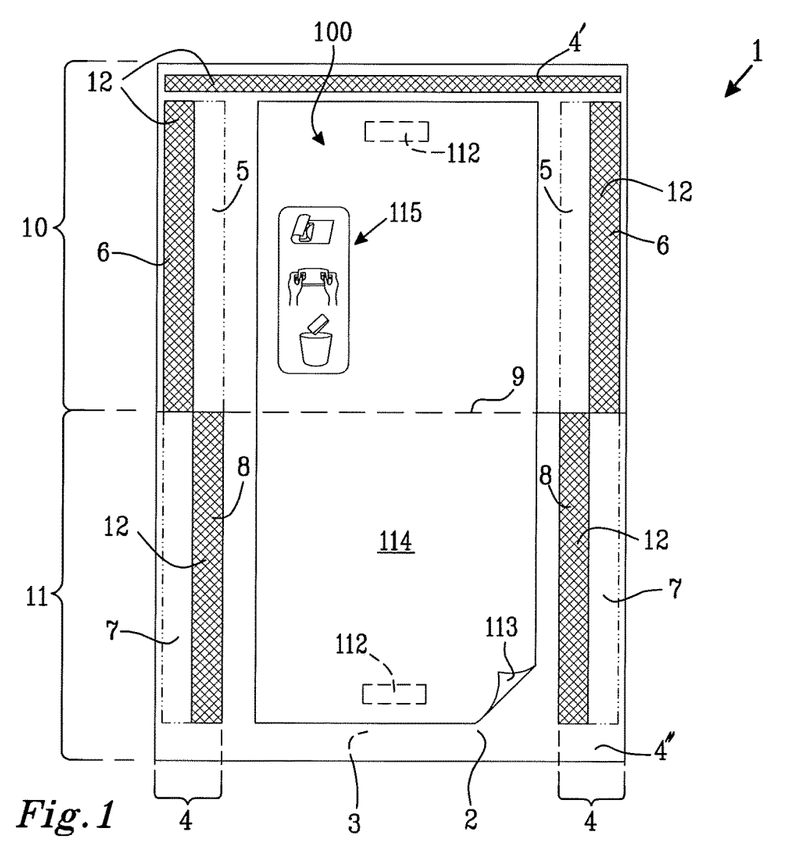
FIG. 1 shows a packaging unit according to an embodiment having one folding axis.
Figure 2:
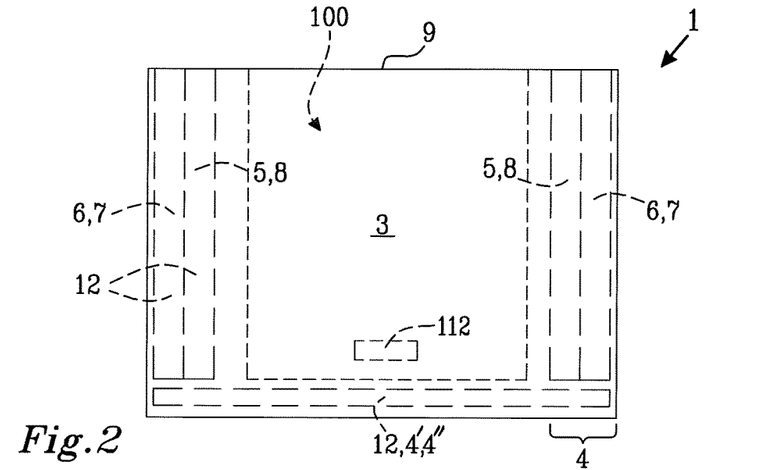
FIG. 2 shows the packaging unit depicted in FIG. 1 in a folded state.

FIG. 1 depicts a packaging unit 1 for hygiene articles according to an embodiment. The packaging unit is formed from a wrap having an inner surface 2 and an outer surface 3, the inner surface comprising an edge zone 4 comprising an inner edge portion 5, 8 and an outer edge portion 6, 7. The wrap also comprises transverse edge zones 4' and 4". The wrap has a folding axis 9, wherein the folding axis divides the sheet into a first region 10 and a second region 11. As shown in FIG. 1, the outer edge portion 6 of the edge zone 4 of the first region 10 is provided with first resealable adhesive 12, while the inner edge portion 5 of the edge zone 4 of the first region 10 is adhesive-free. Further, the inner edge portion 8 of the edge zone 4 of the second region 11 is provided with first resealable adhesive 12, while the outer edge portion 7 of the edge zone 4 of the second region 11 is adhesive-free. Also, the transverse edge zone 4' of the first region 10 is provided with first resealable adhesive 12, while the transverse edge zone 4" of the second region 11 is adhesive-free. Thus, the adhesive pattern in the first region 10 is complementary to the adhesive pattern of the second region 11. This in turn means that, when the wrap is folded about the folding axis 9 as shown in FIG. 2, the edge portions 6 carrying resealable adhesive in the first region 10 are brought in contact with the adhesive-free edge portions 7 in the second region 11, the edge portions 8 carrying resealable adhesive 12 in the second region 11 are brought in contact with the adhesive-free edge portions 5 in the first region 10, and the transverse edge zone 4' carrying resealable adhesive 12 in the first region 10 is brought in contact with the adhesive-free transverse edge zone 4" in the second region 11. As can be seen from FIG. 2, the width of the sealing area corresponds to the sum of the widths of the adhesive-covered portions 6, 8. Such a sealing ensures a tight package for both a new and a disposed article.

Further, according to the present disclosure, the packaging unit 1 further comprises a user prompting device 100, having a user-facing surface 114, and a wrap-facing surface 113. As depicted in FIG. 1, a portion of the wrap-facing surface 113 of the user prompting device 100 is attached to the inner surface 2 of the wrap by means of a second adhesive 112 to thereby bring the wrap-facing surface 113 of the user prompting device 100 into contact with the inner surface of the wrap. The user prompting device 100 comprises a user prompting means 115, arranged on the user-facing surface 114 of the user prompting device 100 and being visible and legible from the user-facing surface 114 of the user prompting device 100. Thus, the user of the packaging unit 1 according to the present disclosure will be prompted to employ the second disposal function of the packaging unit 1.

As may be seen in FIG. 2, the user prompting means 115 is not visible through the outer surface 3 of the wrap, which may be achieved by providing either the wrap or the user prompting device with a sufficient degree of opacity. This is advantageous since the user prompting means 115 would otherwise be visible in reverse through the outer surface 3 of the wrap, something which might be perceived as confusing and disturbing by the user.

Figure 3:
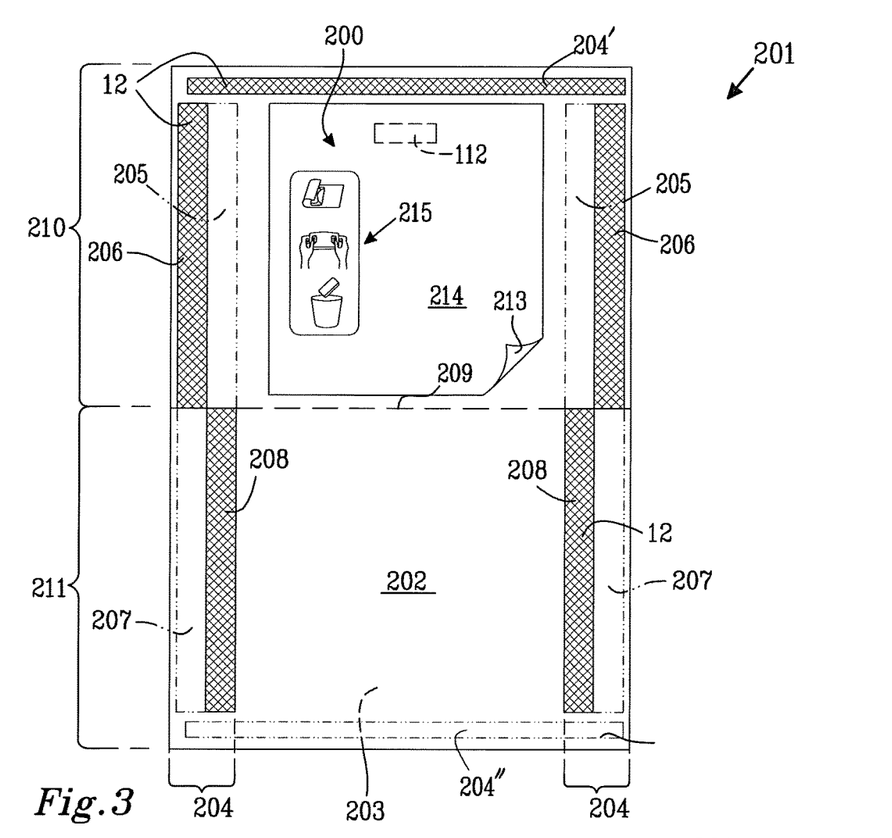
FIG. 3 shows a packaging unit according to an embodiment having one folding axis and a user prompting means visible through the outer surface of the wrap.

FIG. 3 illustrates a packaging unit 201 similar to the one shown in FIG. 1. The packaging unit 201 comprises a user prompting device 200, having a user-facing surface 214, and a wrap-facing surface 213. As depicted in FIG. 3, a portion of the wrap-facing surface 213 of the user prompting device 200 is attached to the inner surface 202 of the wrap by means of a second adhesive 112. The user prompting device 200 comprises a first user prompting means 215, arranged at the user-facing surface 214 of the user prompting device 200, and being visible and legible from the user-facing surface 214 of the user prompting device 200. Thus, the user of the packaging unit 201 according to the present disclosure will be prompted to employ the second disposal function of the packaging unit 201. As may be seen in FIG. 4, the first user prompting means 215 is not visible through the outer surface 203 of the wrap, as described above.

Figure 4:
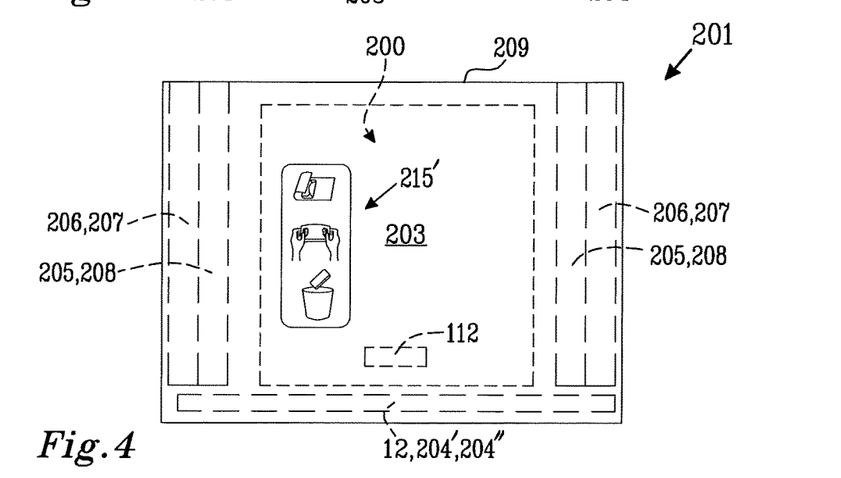
FIG. 4 shows the packaging unit depicted in FIG. 3 in a folded state.

The user prompting device 200 further comprises a second user prompting means 215', as may be seen in FIG. 4, arranged at the wrap-facing surface 213 of the user prompting device 200, and being visible through the outer surface 203 of the wrap. The presence of the second user prompting means 215' has the advantage of prompting the user to employ the second disposal function of the packaging unit 201 prior to extracting a new hygiene article, such that the user is aware of the second disposal function of the packaging unit 201 before the soiled article is removed. Otherwise, there is a risk that the user selects some other way for disposal of the soiled article, before the presence of the second disposal function of the packaging unit becomes apparent to the user.

It is important that the first user prompting means 215 is not visible through the outer surface 203 of the wrap, and that the second user prompting means 215' is not visible through the user-facing surface 214 of the user prompting device. This may for instance be achieved by providing the user prompting device 200 with a sufficient degree of opacity, and printing the first user prompting means 215 on the user-facing surface 214 of the user prompting device 200, and printing the second user prompting means 215' on the wrap-facing surface 213 of the user prompting device 200. The wrap should have sufficient transparency in order to allow the second user prompting means 215' to be visible and legible through the outer surface 203 of the wrap.

Figure 5:
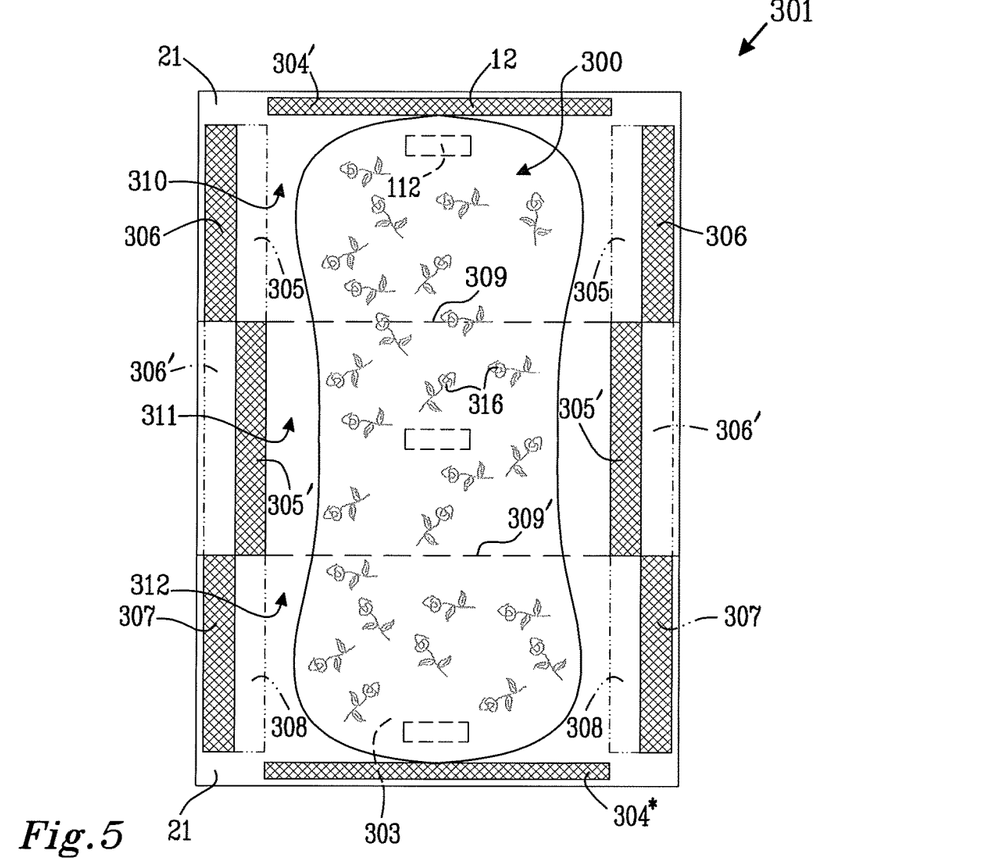
FIG. 5 shows a packaging unit according to an embodiment having two folding axes.
Figure 6:
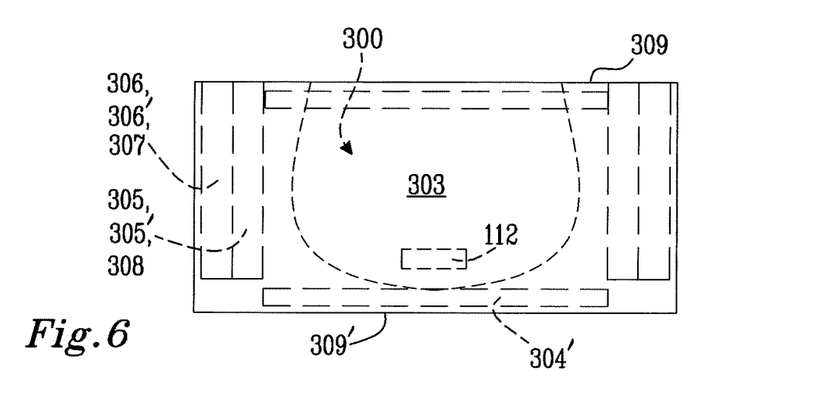
FIG. 6 shows the packaging unit depicted in FIG. 3 in a folded state.

The most common packaging unit for individual packaging of absorbent articles is a rectangular sheet comprising two folding axes, longitudinal edges and transverse edges. Such an embodiment is illustrated in FIG. 5. The packaging unit 301 is a rectangular sheet comprising two folding axes 309, 309' dividing the packaging unit into a first region 310, a second region 311 and a third region 312. Each of the regions comprises an inner edge portion 305, 305', 308 and an outer edge portion 306, 306', 307. As shown in FIG. 5, the outer edge portions 306, 307 of the first and third regions respectively are provided with the first resealable adhesive 12, while the inner edge portions 305, 308 of the first and third regions respectively are adhesive-free. The adhesive pattern of the second region 311 is complementary to the adhesive pattern of the first and third regions 310, 312, thus forming a chessboard pattern. In other words, the outer edge portion 306' of the second region 311 is adhesive-free, and the inner edge portion 305' of the second region 311 is provided with the first resealable adhesive 12. This in turn means that, when the sheet is e-folded about the folding axes 309, 309' as shown in FIG. 6, the outer edge portions 306 of the first region 310 or the outer edge portions 307 of the third region 312 carrying resealable adhesive 12 are brought in contact with the adhesive-free outer edge portions 306' in the second region 311, depending on which of the first and the third regions 310, 312 is brought in contact with the second region 311. Consequently, the inner edge portions 305' carrying resealable adhesive 12 in the second region 311 are brought into contact with the adhesive-free inner edge portions 305 of the first region 310 or the adhesive-free inner edge portions 308 of the third region 312. As can be seen from FIG. 6, the width of the sealing area corresponds to the sum of the widths of the adhesive-covered portions 306, 305'. It should be noted that the order in which the packaging unit is folded is irrelevant. For example, the packaging unit may be folded around the second folding axis 309', bringing the third region 312 in contact with the second region 311, sealing the outer edge portions 307, 306' and the inner edge portions 308, 305'. The packaging unit is subsequently folded around the first folding axis 309', bringing the first region 310 in contact with the outer surface of the third region 312, thus sealing the packaging unit (FIG. 6). The folding order may also be reversed. This is a great advantage, since when the packaging unit of the present disclosure is used for disposal, the user does not have to fold the packaging unit in any particular order to be able to obtain a tightly sealed package. The packaging unit will provide a tight and hygienic package regardless of the folding order.

In order to obtain a tight package, the transverse edge zones 304' and 304* of the packaging unit 301 are provided with resealable adhesive 12. When both transverse edge zones 304' and 304* are provided with resealable adhesive, the folding order is irrelevant, as described above. It is also conceivable to provide only one of the transverse edge zones with resealable adhesive. In this case, the folding is initiated around the folding axis being positioned closest to the adhesive-free transverse edge, such that the region comprising the adhesive-covered transverse edge zone forms a lid and the resealable adhesive positioned at the transverse edge zone seals the packaging unit.

In order to facilitate the opening of the package, the adhesive-covered portions are positioned such that at least one of the corner portions 21 of the packaging unit 301 is adhesive-free, thus forming a gripping tab that is gripped by the user upon opening the package. Moreover, the adhesive-free corner portion 21 serves as an evacuation opening when the packaging unit is sealed (FIG. 6).

It should be noted that when the packaging unit according to the present disclosure is used for disposal, the user can choose to roll up the packaging unit and the soiled article positioned on it rather than folding it.

Further, the packaging unit 301 comprises a user prompting device 300 for prompting the user to employ the second disposal function of the packaging unit 301. As illustrated in FIG. 5, the user prompting means 301 is of substantially the same shape and size as the hygiene article being used together with the packaging unit 301. Thus, the user will prompted to employ the second disposal function of the packaging unit 301 by being guided to place the soiled hygiene article over the user prompting device 301, and then fold or roll the packaging unit 301 in an optional manner. In the embodiment depicted in FIG. 5, the user prompting device 300 comprises print 316, giving the user prompting device 300 a more aesthetical appearance.

Although the present disclosure has been described with reference to various embodiments, those skilled in the art will recognise that changes may be made without departing from the scope of the present disclosure. It is intended that the detailed description be regarded as illustrative and that the appended claims including all the equivalents are intended to define the scope of the present disclosure.

The invention claimed is:

1. A packaging unit for hygiene articles, comprising a wrap formed from a sheet of material, said wrap having an inner and an outer surface, said inner surface comprising an edge zone comprising an inner edge portion and an outer edge portion, said wrap having at least one folding axis, said at least one folding axis dividing said wrap into a first region and a second region, wherein one of said inner edge portion and said outer edge portion of said edge zone of said first region is provided with a first resealable adhesive, and the other of said inner edge portion and said outer edge portion of said edge zone of said first region is adhesive-free; wherein one of said inner edge portion and said outer edge portion of said edge zone of said second region is provided with said first resealable adhesive, and the other of said inner edge portion and said outer edge portion of said edge zone of said second region is adhesive-free in a complementary manner to said edge zone of said first region, such that when said wrap is folded about said at least one folding axis, said one of the inner edge portion and the outer edge portion carrying said first resealable adhesive in said first region is brought in contact with said one of the inner edge portion and the outer edge portion that is adhesive-free in said second region, and said one of the inner edge portion and the outer edge portion carrying said first resealable adhesive in said second region is brought in contact with said one of the inner edge portion and the outer edge portion that is adhesive-free in said first region, said packaging unit configured to have a first packaging function as a packaging wrap for a non-used article, and a second disposal function as a disposal wrap for a used article, wherein said packaging unit further comprises a user prompting device having a wrap-facing surface and a user-facing surface, wherein said user prompting device is permanently attached to said wrap such that at least a portion of said wrap-facing surface of said user prompting device is in contact with said inner surface of said wrap, and said user prompting device is configured to prompt the user to employ said second disposal function, wherein said user prompting device comprises user prompting means being visible and legible from said user-facing surface of said user prompting device.

2. The packaging unit according to claim 1, wherein said user prompting means is printed on at least one of the user-facing surface of said user prompting device and the wrap-facing surface of said user prompting device.

3. The packaging unit according to claim 1, wherein said user prompting device is opaque.

4. The packaging unit according to claim 1, wherein said user prompting device comprises a release liner.

5. The packaging unit according to claim 4, wherein said release liner is manufactured from one of paper, non-woven and plastic film material.

6. The packaging unit according to claim 1, wherein said user prompting device is silicone-coated on said user-facing surface of said user prompting device.

7. A packaging unit according to claim 1, wherein a longitudinal extension of said user prompting device is 60-100% of a longitudinal extension of said wrap.

8. A packaging unit according to claim 1, wherein said sheet of material is of substantially rectangular shape and comprises longitudinal edges, transverse edges and corner portions, said edge zone of said first region and said edge zone of said second region of said sheet of material being arranged along said longitudinal edges.

9. The packaging unit according to claim 8, wherein said sheet of material comprises transverse edge zones and wherein at least a portion of at least one of said transverse edge zones is provided with said first resealable adhesive.

10. The packaging unit according to claim 8, wherein a portion of a transverse edge zone of said first region is provided with said first resealable adhesive, and a remaining portion of said transverse edge zone of said first region is adhesive-free, and a portion of a transverse edge zone of said second region is provided with said first resealable adhesive, and a remaining portion of said transverse edge zone of said second region is adhesive-free in a complementary manner to said transverse edge zone of said first region such that when said sheet of material is folded about said at least one folding axis, said transverse edge zone carrying said first resealable adhesive in said first region is brought in contact with said adhesive-free transverse edge zone in said second region, and said transverse edge zone carrying said first resealable adhesive in said second region is brought in contact with said adhesive-free transverse edge zone in said first region.

11. The packaging unit according to claim 8, wherein at least one of said corner portions is free from said first resealable adhesive such that a gripping tab is formed.

12. The packaging unit according to claim 8, wherein said sheet of material has two folding axes dividing said sheet of material into said first region, said second region and a third region.

13. The packaging unit according to claim 12, wherein said sheet of material is folded along said two folding axes with said first region, said second region and said third region in an overlapping configuration.

14. The packaging unit according to claim 12, wherein an edge portion of an edge zone of said third region is provided with said first resealable adhesive corresponding to the edge portion of said edge zone of said first region provided with said first resealable adhesive, and is complementary to the edge portion of said edge zone of said second region provided with said first resealable adhesive, such that a chessboard pattern of said first resealable adhesive is formed along each of said longitudinal edges.

15. The packaging unit according to claim 14, wherein a width of the edge portions of two adjacent ones of the first region, the second region and the third region that are provided with the first resealable adhesive is dimidiated compared to a width of the remaining one of the first region, the second region and the third region that are provided with the first resealable adhesive.

16. The packaging unit according to claim 12, wherein at least a portion of one of said transverse edge zones is provided with said first resealable adhesive.

17. The packaging unit according to claim 1, wherein said wrap is at least one of being opaque and comprising print.

18. The packaging unit according to claim 1, wherein said first resealable adhesive is a pressure-sensitive adhesive with unlimited open time.

19. A packaged disposable hygiene article comprising:
a packaging unit according to claim 1; and
a hygiene article releasably affixed to said user prompting device.

20. A method of forming a packaging unit for hygiene articles from a sheet of material, said packaging unit configured to have a first packaging function as a packaging wrap for a non-used article, and a second disposal function as a disposal wrap for a used article, said method comprising the steps of:
   a. providing a sheet having an inner surface and an outer surface, said inner surface comprising an edge zone comprising an inner edge portion and an outer edge portion, said sheet having a first folding axis, said first folding axis dividing said sheet into a first region and a second region, wherein said first region comprises a first central portion, and said second region comprises a second central portion;
   b. providing one of said inner edge portion and said outer edge portion of said edge zone of said first region with a first resealable adhesive, such that the other of said inner edge portion and said outer edge portion of said edge zone of said first region is adhesive-free;
   c. providing one of said inner edge portion and said outer edge portion of said edge zone of said second region with said first resealable adhesive, such that the other of said inner edge portion and said outer edge portion of said edge zone of said second region is adhesive-free in a complementary manner to said edge zone of said first region; and
   d. providing said inner surface of said sheet with a user prompting device having a wrap-facing surface and a user-facing surface, wherein said user prompting device comprises user prompting means being visible and legible from said user-facing surface of said user prompting device, and said user prompting device is configured to prompt the user to employ said second disposal function.

21. The method according to claim 20, wherein steps b and c occur simultaneously.

22. The method according to any one of claim 20, further comprising the steps of:
   e. providing at least one of said first central portion of said first region and said second central portion of said second region with a second adhesive;
   f. bringing said wrap-facing surface of said user prompting device in contact with said inner surface of said sheet such that at least a portion of said wrap-facing surface of said user prompting device becomes permanently attached to said inner surface of said sheet in at least said first central portion and said second central portion provided with said second adhesive by means of said second adhesive; wherein
steps e and f occur after step a but before step d.

23. The method according to claim 22, wherein step e occurs simultaneously with steps b and c.

24. The method according to claim 20, further comprising the steps of:
   g. releasably affixing a hygiene article to said user-facing surface of said user prompting device;
   folding the sheet about said first folding axis, such that the one of said inner edge portion and said outer edge portion carrying said first resealable adhesive in said first region is brought in contact with the one of said inner edge portion and said outer edge portion that is adhesive-free in said second region, and the one of said inner edge portion and said outer edge portion carrying said first resealable adhesive in said second region is brought in contact with the one of said inner edge portion and said outer edge portion that is adhesive-free at said first region.

25. The method according to claim 24, wherein step g occurs immediately before step d.

26. The method according to claim 24, further comprising the step of:
   i. providing said user-facing surface of said user prompting device with a third resealable adhesive;
   wherein step i occurs immediately before step g.

27. The method according to claim 20, wherein said sheet has said first folding axis and a second folding axes dividing said sheet into said first region, said second region and a third region, and the method further comprising the steps of:
   j. providing a portion of an edge zone of said third region with said first resealable adhesive; and
   k. folding said sheet about said second folding axis such that an inner surface of said third region is brought in contact with an outer surface of said first region,
   wherein step j occurs after step a but before step d, and step k occurs after step h.

28. The method according to claim 27, wherein step j occurs simultaneously with steps b and c.

* * * * *

UNITED STATES PATENT AND TRADEMARK OFFICE
CERTIFICATE OF CORRECTION

| | |
|---|---|
| PATENT NO. | : 10,285,877 B2 |
| APPLICATION NO. | : 15/318216 |
| DATED | : May 14, 2019 |
| INVENTOR(S) | : Conny Dahlqvist, Ulrika Persson and Sofia Ekstedt |

It is certified that error appears in the above-identified patent and that said Letters Patent is hereby corrected as shown below:

On the Title Page

"(73) ESSITY HYGIENE AND HEALTH AKTIEBOLAG AB"

Should read:
--(73) ESSITY HYGIENE AND HEALTH AKTIEBOLAG--

Signed and Sealed this
Fourteenth Day of February, 2023

*Katherine Kelly Vidal*

Katherine Kelly Vidal
*Director of the United States Patent and Trademark Office*